(12) United States Patent
Wang et al.

(10) Patent No.: US 11,960,797 B2
(45) Date of Patent: Apr. 16, 2024

(54) DYNAMIC BUILDING FLOORPLANS USING RETRACTABLE PARTITIONS

(71) Applicant: International Business Machines Corporation, Armonk, NY (US)

(72) Inventors: Xinlin Wang, Irvine, CA (US); Lisa Seacat DeLuca, Bozeman, MT (US)

(73) Assignee: International Business Machines Corporation, Armonk, NY (US)

( * ) Notice: Subject to any disclaimer, the term of this patent is extended or adjusted under 35 U.S.C. 154(b) by 715 days.

(21) Appl. No.: 17/125,446

(22) Filed: Dec. 17, 2020

(65) Prior Publication Data
US 2022/0198080 A1    Jun. 23, 2022

(51) Int. Cl.
*G06F 30/13* (2020.01)
*G16H 50/30* (2018.01)

(52) U.S. Cl.
CPC ............. *G06F 30/13* (2020.01); *G16H 50/30* (2018.01)

(58) Field of Classification Search
CPC ......... G06F 30/00; G06F 30/13; G16H 50/30; G06Q 10/02; G06Q 10/10
USPC ............................................................. 703/1
See application file for complete search history.

(56) References Cited

U.S. PATENT DOCUMENTS

| | | | |
|---|---|---|---|
| 5,651,219 A | 7/1997 | Baloga | |
| 7,348,736 B2 | 3/2008 | Piepgras | |
| 2005/0011138 A1 | 1/2005 | Ball | |
| 2005/0016081 A1 | 1/2005 | Gomree | |
| 2017/0177747 A1* | 6/2017 | Atherton | G06F 30/13 |
| 2017/0328127 A1* | 11/2017 | Stathis | F21S 6/003 |

OTHER PUBLICATIONS

"Sliding Pocket Wall (SPW)", Vimeo, last printed Nov. 3, 2020, 1 page, <https://vimeo.com/154747513>.
"Smartglass Can Fade From Translucent to Opaque in a Second", YouTube, Dec. 10, 2017, 1 page, <https://www.youtube.com/watch?v=G_6DfedKqWU>.
Febretti, et al. "Omegalib: a Multi-View Application Framework for Hybrid Reality Display Environments", 2014 IEEE Virtual Reality (VR), pp. 9-14.

(Continued)

*Primary Examiner* — Cedric Johnson
(74) *Attorney, Agent, or Firm* — Stephen R. Yoder

(57) ABSTRACT

Disclosed are techniques for managing retractable privacy partitions to dynamically subdivide spaces in buildings into sub-spaces (or rooms). Retractable privacy partitions are distributed throughout a given space in a building such that the retractable privacy partitions can completely retract into a surface of the given space (for example, the floor or ceiling) such that when they are fully extended, the retractable privacy partitions create separate rooms within the given space, and when fully retracted, the retractable privacy partitions do not significantly impede movement or sightlines throughout the given space. Further disclosed are techniques to manage the retractable privacy partitions based on properties indicative of demand for rooms of various sizes within the given space. Some embodiments further disclose retractable privacy partitions including switchable glass to provide additional flexibility through dynamic opacity along with dynamic extension/retraction of the partitions.

17 Claims, 10 Drawing Sheets

(56) References Cited

OTHER PUBLICATIONS

Ladner, et al., "A Distributed Virtual Reality Prototype for Real Time GPS Data", 1Naval Research Laboratory, May 2000, 7 pages.

Mallasi, Zaki, "Dynamic quantification and analysis of the construction workspace congestion utilising 4D visualisation", Automation in Construction, 2006, vol. 15.5, pp. 640-655.

Microsoft 365 Team, "How to effectively lay out space with floor plan software", Microsoft Business Tech, Sep. 20, 2019, 5 pages, <https://www.microsoft.com/en-us/microsoft-365/business-insights-ideas/resources/how-to-effectively-lay-out-space-with-floor-plan-software>.

Ohta, Takashi, "Dynamically Reconfigurable Multi-Display Environment for CG Contents", Proceedings of the 2008 International Conference on Advances in Computer Entertainment Technology, 2008, p. 416.

Sherstyuk, et al., "Virtual Roommates: Sampling and Reconstructing Presence in Multiple Shared Spaces", Handbook of Augmented Reality, © Springer Science+Business Media, LLC, 2011, pp. 211-230.

Staff Writer, "Elevate Your Office Space with Switchable Glass Panels", Thomas, Jul. 19, 2018, 3 pages, <https://www.thomasnet.com/insights/elevate-your-office-space-with-switchable-glass-panels/>.

\* cited by examiner

DYNAMIC BUILDING FLOORPLANS USING RETRACTABLE PARTITIONS

BACKGROUND

The present invention relates generally to the field of office building management systems, and more particularly to creating and operating dynamic floorplans for buildings using retractable partitions. As used in this document, the term floorplan is hereby defined to mean any set of computer data that represents the physical features (for example, walls, doors, other fixtures) of the physical space of at least a portion of a structure (for example, a building); "floorplans" are not limited to representations of the physical space that are in the form of scale diagrams; "floorplans" are not limited to representations of the arrangement of rooms in one story of a building structure.

In architecture and building engineering, a floor plan is a graphic, drafted to scale, showing a view from above, of the relationships between rooms, spaces, traffic patterns, and other physical features at one level of a given structure.

Smart glass, also known as switchable glass (additionally as smart windows or switchable windows in those applications) is a glass or glazing whose light transmission properties are altered when voltage, light, or heat is applied. In general, the glass changes from transparent or translucent to opaque and vice versa, changing from letting light pass through to blocking some (or all) wavelengths of light and vice versa. Different types smart glass technologies include electrochromic, photochromic, thermochromic, suspended-particle, micro-blind, and polymer-dispersed liquid-crystal devices.

SUMMARY

According to an aspect of the present invention, there is a method, computer program product and/or system for use with a portion of floorspace of a building with a plurality of retractable privacy partitions throughout the portion of the floorspace that performs the following operations (not necessarily in the following order): (i) receiving a floorplan requirements dataset indicating floorspace requirements corresponding to quantities of at least one type of room needed within the portion of floorspace of the building; and (ii) determining an updated floorplan for the portion of floorspace of the building, based, at least in part, on the floorplan requirements dataset, where the updated floorplan includes a plurality of rooms of at least one type of room defined by at least partially extending at least some of the plurality of retractable privacy partitions and completely retracting at least some of the plurality of retractable privacy partitions.

DETAILED DESCRIPTION

Figure 1:
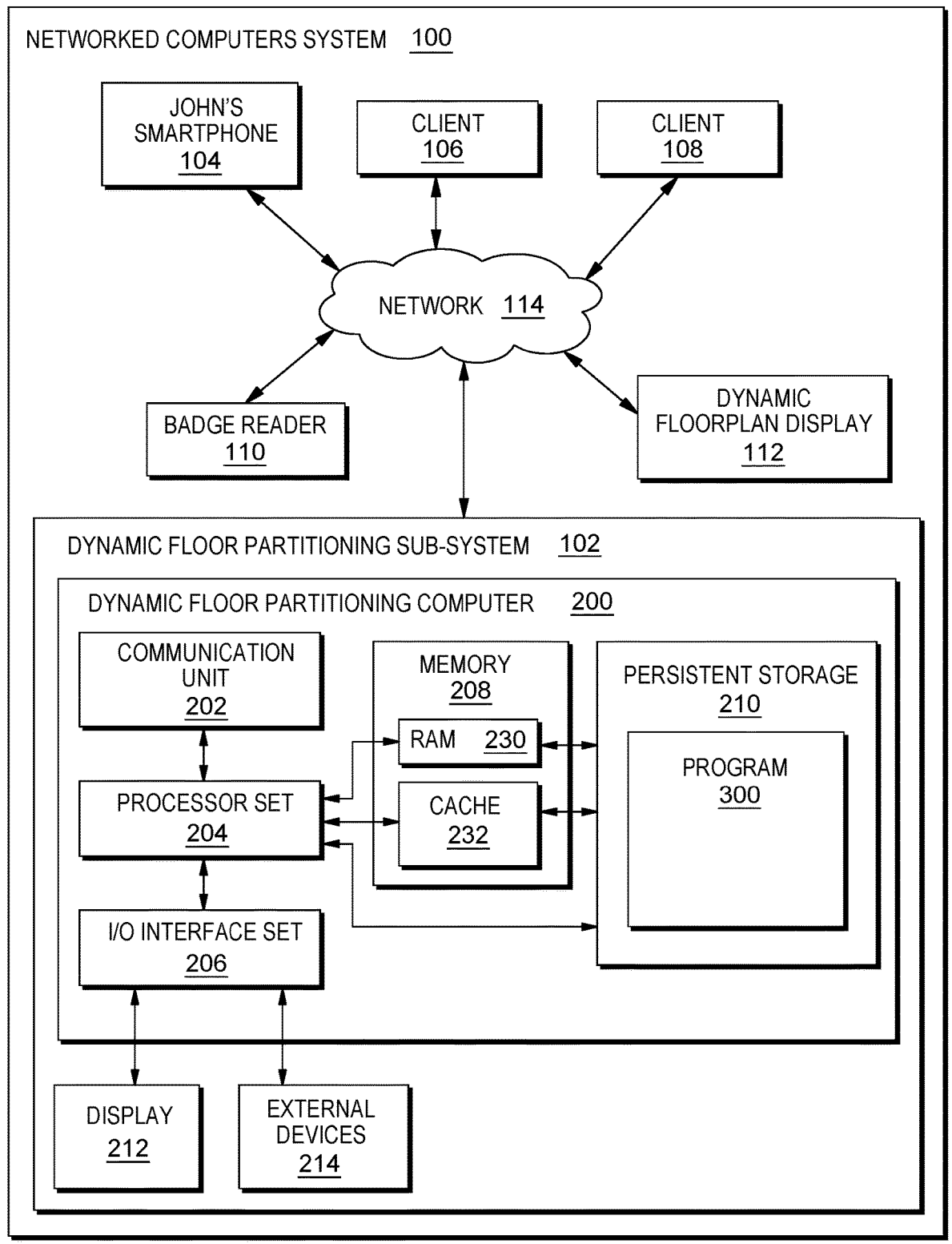
FIG. 1 is a block diagram view of a first embodiment of a system according to the present invention.

Some embodiments of the present invention are directed to techniques for managing retractable privacy partitions to dynamically subdivide spaces in buildings into sub-spaces (or rooms). Retractable privacy partitions are distributed throughout a given space in a building such that the retractable privacy partitions can completely retract into a surface of the given space (for example, the floor or ceiling) such that when they are fully extended, the retractable privacy partitions create separate rooms within the given space, and when fully retracted, the retractable privacy partitions do not significantly impede movement or sightlines throughout the given space. Further disclosed are techniques to manage the retractable privacy partitions based on properties indicative of demand for rooms of various sizes within the given space. Some embodiments further disclose retractable privacy partitions including switchable glass to provide additional flexibility through dynamic opacity along with dynamic extension/retraction of the partitions.

This Detailed Description section is divided into the following subsections: (i) The Hardware and Software Environment; (ii) Example Embodiment; (iii) Further Comments and/or Embodiments; and (iv) Definitions.

I. THE HARDWARE AND SOFTWARE ENVIRONMENT

The present invention may be a system, a method, and/or a computer program product. The computer program product may include a computer readable storage medium (or media) having computer readable program instructions thereon for causing a processor to carry out aspects of the present invention.

The computer readable storage medium sometimes referred to as a machine readable storage device, can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be any thing made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in FIG. 1, networked computers system 100 is an embodiment of a hardware and software environment for use with various embodiments of the present invention. Networked computers system 100 includes: server subsystem 102 (sometimes herein referred to, more simply, as subsystem 102); John's smartphone 104; client subsystems 106, 108; badge reader 110; dynamic floorplan display 112; and communication network 114. Server subsystem 102 includes: server computer 200; communication unit 202; processor set 204; input/output (I/O) interface set 206; memory 208; persistent storage 210; display 212; external device(s) 214; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with server computer 200. For example, I/O interface set 206 provides a connection to external device set 214. External devices 214 will typically include devices such as a keyboard, keypad, a touch screen, and/or some other suitable input device. External devices 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

John's smartphone 104 is a typical smartphone device, with a touchscreen display attached to a handheld computer device with wireless communication capabilities.

Badge reader 110 is a badge reader device capable of electronically reading badge information from identification badges presented to it (either by swiping through a typical electronic badge reader, holding up to a camera to visually read the information, or holding a badge proximate to an RFID reader).

Dynamic floorplan display 112 is a computer device with a connected touchscreen display device (not shown).

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. EXAMPLE EMBODIMENT

Figure 2:
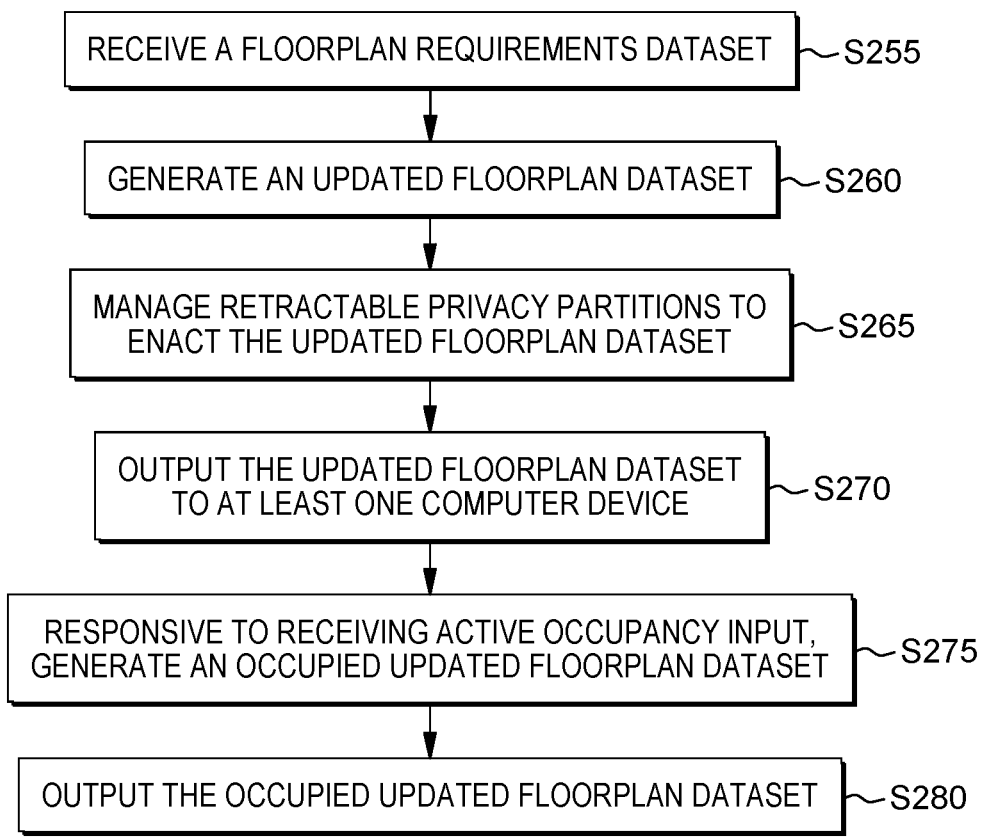
FIG. 2 is a flowchart showing a first embodiment method performed, at least in part, by the first embodiment system.
Figure 3:
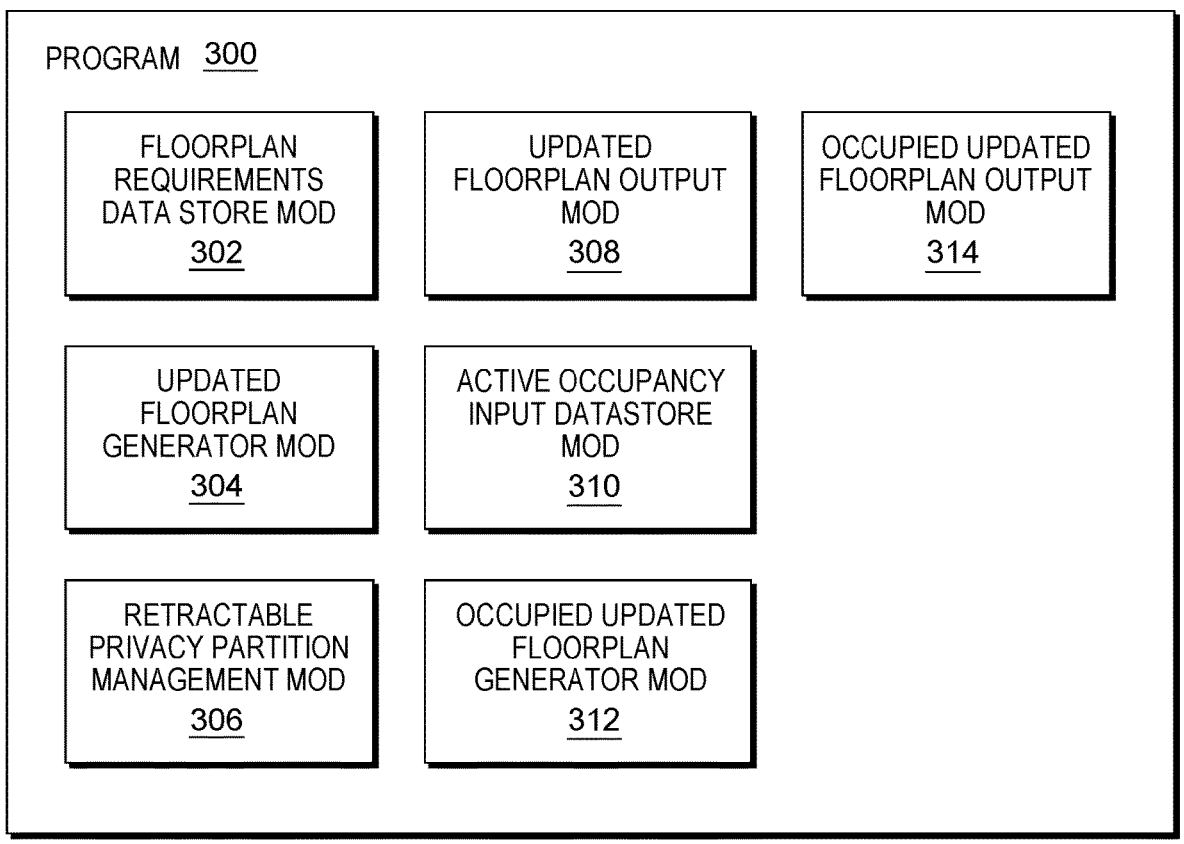
FIG. 3 is a block diagram showing a machine logic (for example, software) portion of the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or control performance of at least some of the method operations of flowchart 250. This method and associated software will now be discussed, over the course of the following paragraphs, with extensive reference to the blocks of FIGS. 1, 2, 3, 4A and 4B.

Processing begins at operation S255, where floorplan requirements datastore module ("mod") 302 receives a floorplan requirements dataset. In this simplified embodiment, the floorplan requirements dataset includes information about a portion of a building with dynamic floorplan capabilities, where the portion of the building is an area of the floor/floorspace of one story of the building where there are a plurality of retractable privacy partitions arranged in a grid-like pattern. This grid-like pattern consists of subportions of the floor bounded by a square of retractable privacy partitions, with one on each side, or what may alternatively be referred to as a "unit room." A unit room is the smallest type of room that may be formed by the retractable privacy partitions. Larger rooms may be formed by combining a number of unit rooms and completely retracting into the floor the retractable privacy partitions that would separate each unit room from their respective adjacent unit rooms. The retractable privacy partitions are room partitions with two segments and a motor that is electronically operated to extend and retract one or both segments of the partition out of or completely into the floor, such that the top of the retractable privacy partition is mostly flush with the adjacent floor when completely retracted into the floor, and when fully extended forms a floor-to-ceiling wall. Each retractable privacy partition includes a wireless communication module that receives machine instructions to operate the retractable privacy partition (for example, extending or retracting the segments of the partition) and sends state information corresponding to the status of the retractable privacy partition (such as which segments are extended, whether they are completely or partially extended, completely retracted into the floor, etc.).

In this simplified embodiment, the floorplan requirements dataset corresponds to the entire first story of an office building called "Example Office Building" and includes information indicating quantities of rooms that are required, namely that four unit room size offices and one conference room is required for the day, where the conference room is to be four unit rooms in size. Example Office Building is the headquarters for Example Corp., a corporation headed by John Doe that employs three other employees. Included with the floorplan requirements dataset is a calendar indicating how many employees are reporting to Example Office Building for the day and if there are any meetings requiring a conference room. The calendar indicates that there will be four employees reporting to Example Office Building and meetings with clients throughout the day. In this example embodiment, the floorplan requirements dataset is sent from client 106, a server client owned and operated by Example Corp. that hosts a centralized calendar for John and all of the employees of Example Corp.

In some alternative embodiments, the floorplan requirements dataset corresponds to different buildings and different portions of different stories of said different buildings, including only portions of some stories or several different stories, up to and including the entirety of every story of a building. In some alternative embodiments, the retractable privacy partitions are made of switchable glass. In some of those alternative embodiments, the switchable glass is electrochromic, where a computer (such as John's smartphone 104) can provide input to another computer connected to the retractable privacy partition to indicate how transparent or opaque the retractable privacy partition should be. In some alternative embodiments, the transparency/opacity can be adjusted independently for each segment of a given partition.

Processing proceeds to operation S260, where updated floorplan generator mod 304 generates an updated floorplan dataset. In this simplified embodiment, using the floorplan requirements dataset stored in floorplan requirements datastore mod 302, updated floorplan generator mod 304 generates an updated floorplan dataset that includes four unit room sized cubicles and one conference room. This updated floorplan is shown in window 402A of screenshot 400A of FIG. 4A, where cubicles 404A, 406A, 408A and 410A are present, as well as conference room A 402A. If a conference room is not needed on a given day, the floorplan requirements dataset might indicate a floorplan that includes additional cubicles in the place of conference room A. The updated floorplan dataset includes a series of machine instructions for instructing the extension and retraction of various retractable privacy partitions across the first story of Example Office Building to provide for the appropriate arrangement of rooms indicated by the floorplan requirements dataset.

Processing proceeds to operation S265, where retractable privacy partition management mod 306 manages retractable privacy partitions to enact the updated floorplan dataset. In this simplified embodiment, using the machine instructions included in the updated floorplan dataset, retractable privacy partition management mod 306 extends several retractable privacy partitions surrounding cubicles shown in FIG. 4A as 404A, 406A, 408A and 410A, with each partition extended such that one of the two segments is fully extended from the floor and the other segment rests within the other segment. Retractable privacy partitions surrounding the borders of conference room A 402A are fully extended to the ceiling, and partitions that are not part of the perimeter of conference room A 402A are completely retracted into the floor of Example Office Building.

Figure 4A:
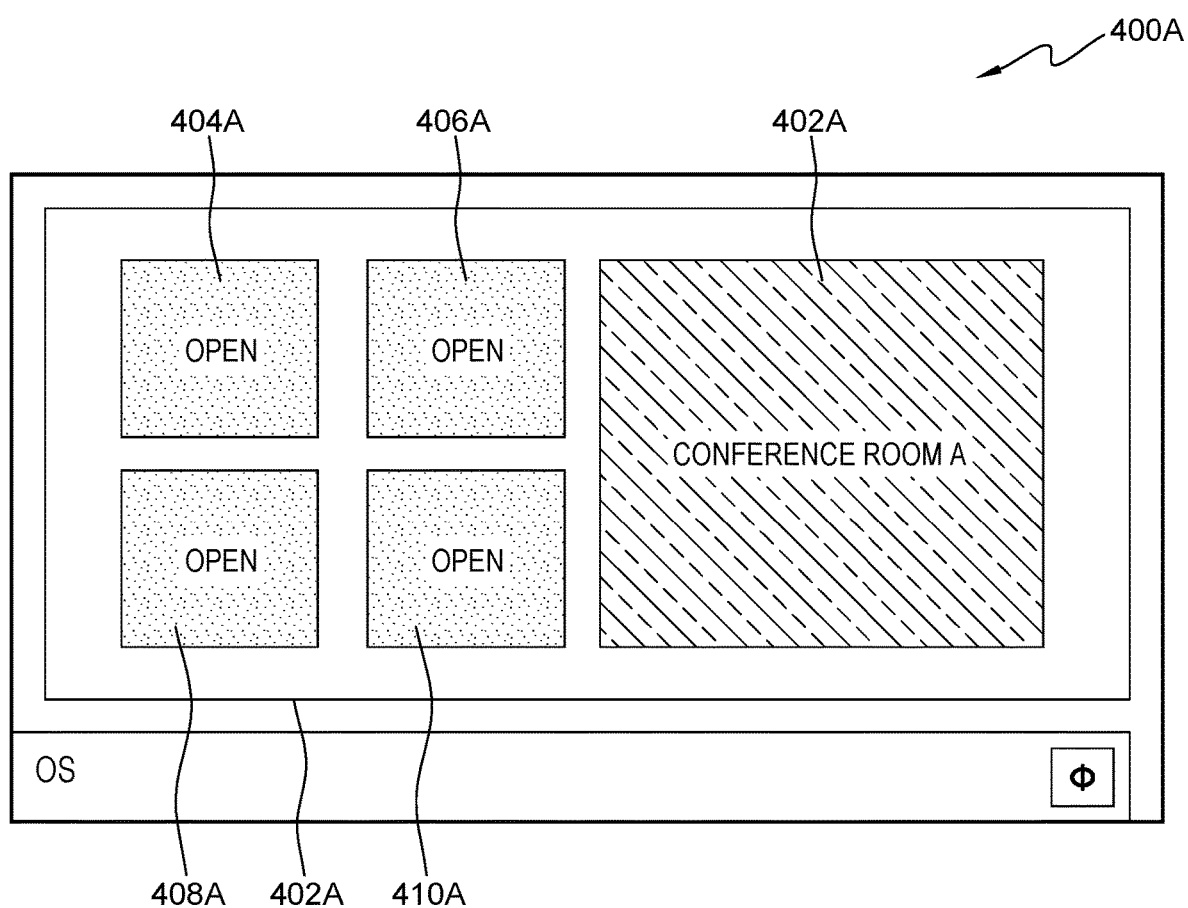
FIG. 4A is a screenshot view generated by the first embodiment system.
Figure 4B:
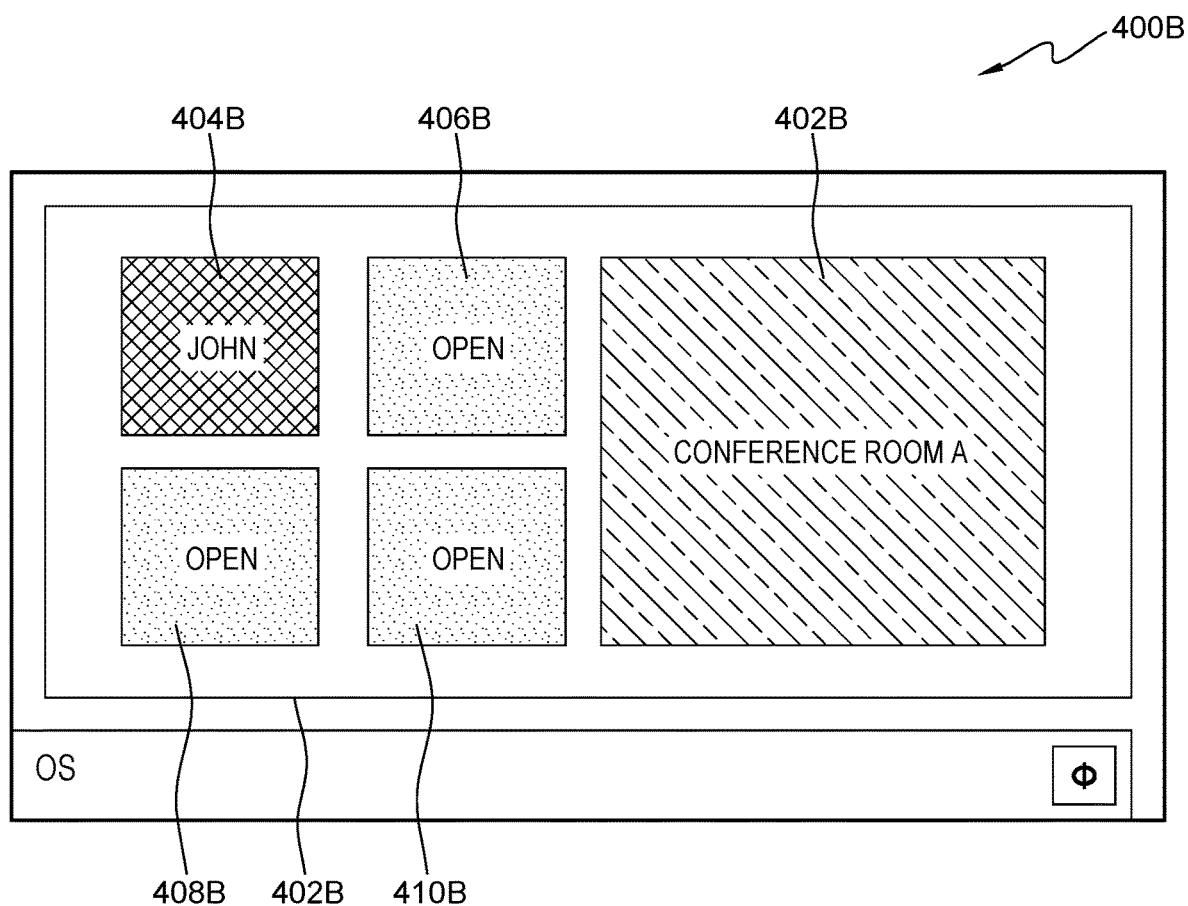
FIG. 4B is a screenshot view generated by the first embodiment system.

Processing proceeds to operation S270, where updated floorplan output mod 308 outputs the updated floorplan dataset to at least one computer device. In this simplified embodiment, the updated floorplan dataset is outputted over network 114 of FIG. 1 as a visual floorplan as shown in screenshot 400A of FIG. 4A to dynamic floorplan display 112 of FIG. 1. Dynamic floorplan display 112 is located inside of Example Office Building near the entrance, providing a graphic representation of the updated floorplan of the first story of Example Office Building. The visual floorplan is also sent to John's Smartphone 104 over network 114, so that John Doe can view the floorplan on his way into work. In some alternative embodiments, a version of the outputted updated floorplan accessible for the visually impaired is provided by outputting, using text-to-speech techniques, audio information corresponding to a voice reading out the updated floorplan in the updated floorplan dataset using a notation based on horizontal and vertical coordinates corresponding to room units, such as (cubicle at 1H,1V for a cubicle at a first horizontal, first vertical position). In some alternative embodiments, the visual floorplan, as in screenshot 400A of FIG. 4A, is outputted over network 114 to client 108, where client 108 is a personal computer device associated with an employee of Example Corp.

Processing proceeds to operation S275, where occupied updated floorplan generator mod 312, responsive to receiving active occupancy input in active occupancy input datastore mod 310, generates an occupied updated floorplan dataset. In this simplified embodiment, John Doe is the first person into Example Office Building to report for work for the day. John provides active occupancy input indicating which cubicle he is reserving for himself by first swiping his identification badge through badge reader 110 of FIG. 1, which provides identification information to dynamic floorplan display 112 over network 114 indicating which employee of Example Corp. is reserving a cubicle. Dynamic floorplan display 112, displaying the updated floorplan as in S270, receives touchscreen input selecting cubicle 404A of FIG. 4A, which is correlated with the identification information from badge reader 110 and stored in active occupancy input datastore mod 310. In response to this input, occupied updated floorplan generator mod 312 generates an occupied updated floorplan dataset indicating that John Doe has reserved cubicle 404A of FIG. 4A.

Processing proceeds to operation S280, where occupied updated floorplan output mod 314 outputs the occupied updated floorplan dataset. In this simplified embodiment, occupied updated floorplan output mod 314 outputs the occupied updated floorplan dataset as a visual floorplan as shown in screenshot 400B of FIG. 4B to dynamic floorplan display 112 of FIG. 1, replacing the previous updated floorplan shown in screenshot 400A of FIG. 4A. Screenshot 400B now showing cubicle 404B as occupied by John Doe (indicated simply as JOHN), while cubicles 406B, 408B and 410B remain open and available for reservation. Conference room A is still indicated as present in the floorplan, unchanged from the updated floorplan dataset and shown as 402B. In some alternative embodiments, the occupied updated floorplan dataset is also sent to John's smartphone 104 each time a new occupied updated floorplan dataset is generated, such as each time another employee of Example Corp. reserves a cubicle.

In yet other alternative embodiments, persons who reserve rooms formed from the retractable privacy partitions may, depending on their organizational privileges or permissions (privileges or permissions provided to them by an organization associated with the building implementing the embodiment of the present invention), may operate some of the features of the retractable privacy partitions that are either part of the perimeter of the room that they reserved or exist within the room that they reserved. For example, they may partially lower or raise some or all of the retractable privacy partitions. In instances where the retractable privacy partitions are made of switchable glass, they may adjust the transparency/opacity of the retractable privacy partitions. Where each retractable privacy partition is made of a plurality of segments of switchable glass, transparency/opacity for each segment may be controlled independently of the other segments, enabling simultaneous operation of some segments to be completely transparent, some segments completely opaque, and some segments as in-between stages between completely transparent and completely opaque. In further alternative embodiments, details corresponding to occupants in adjacent "rooms" are compared, using the information used to "reserve a room" to determine if they are on the same team or working on the same project. If such is determined, retractable privacy partitions might be lowered either partially or completely to facilitate interpersonal communication between the occupants working on the same team or project. In other alternative embodiments, other types of details are compared.

III. FURTHER COMMENTS AND/OR EMBODIMENTS

Some embodiments of the present invention recognize the following facts, potential problems and/or potential areas for improvement with respect to the current state of the art: (i) a floorplan of an office building is generated during a design phase before the construction or renovation start; (ii) while there are movable walls which can be used to re-divide a space into different rooms based on the new a floor plan, it takes time to do this kind of renovation and during the renovation, the building cannot be used; (iii) the second problem of the fixed floorplan is that the office space is not fully utilized; (iv) in a modern office building, there are conference rooms (closed area), cubicle areas (open), agile spaces (could be open or close area, but it is different from traditional conference); (v) some of the office buildings may also have one or more big open spaces, such as auditoriums or large classrooms for big seminars or organization all-hands meetings; (vi) it is typical to expect a range for the number of employees working in this kind of office space in order to make sure everyone has a cubicle space and enough conference room space for people to meet; (vii) usually enough regular cubicles (everyone has their own "seat") and a decent number of conference rooms and agile places are built; (viii) this led to 30-50% of the office space is empty through the day in some instances; and (ix) there is a need for dynamically "converting" the office spaces into different number of function blocks (such as individual cubicles, small private rooms, conference room, auditorium . . . ) based on the day to day office space usage demand.

Some embodiments of the present invention recognize the following facts, potential problems and/or potential areas for improvement with respect to the current state of the art: (i) some technologies are available that may be used to divide each functional area on the floor; (ii) for example, a smart-glass material which can fade from translucent to opaque in a second; (iii) switchable glass panels; (iv) pocket doors that can rise out of the ground or out of a wall panel; (v) sound insulation glass with an air gap in the windows/glass material, as well as many other suitable sound insulation materials are available for use; (vi) multiple LED-based lighting units arranged in a personal workspace may be conveniently controlled by an occupant of the workspace to customize or personalize workspace lighting; (vii) workspace customization, including lighting conditions, further is facilitated by various power distribution schemes to allow convenient access to power in the workspace for lighting units and other electronic devices; and (viii) workspace dividers, partitions and walls may be particularly configured to accommodate power distribution systems and various components of networked lighting systems in the workspace environment.

Some embodiments of the present invention may include one, or more, of the following operations, features, characteristics and/or advantages: (i) complete floor plan adjustment and movement of autonomous spaces; (ii) dynamically configure a building floorplan with a number of functional areas/blocks (such as enclosed office space, conference room, open cubical area, a big classroom) to: (a) improve the building space utilization rate, (b) fast change the building floor plan based on the demand, and (c) deliver a better user experience; (iii) space occupancy planning while continuing to find ways to improve employee experiences in offices; (iv) this will help dramatically improve the building space utilization rate; (v) furniture that is not capable of self-rearranging is taken into account for any adjustments to partitions as taught in some embodiments; (vi) smart furniture pieces that can rearrange themselves where a number of smaller desks might come together for a larger conference room are used; (vii) movement of larger pieces would still be a manual process; (viii) extending/retracting privacy partitions based on a health index; (ix) there are a number of ways this can be done; (x) using existing wearable devices, track health information from individuals entering/reserving rooms; (xi) opted-in mobile applications where individuals respond to a questionnaire on their symptoms, which are used to automatically extend/retract some partitions based on their answers; (xii) for wearables, examples of health monitoring sensors include: (a) activity level, (b) time spent sedentary, (c) number of steps taken, (d) sleep patterns, (e) resting heart rate, (f) heart rate variability, (g) stress level, (h) body temperature, and (i) blood oxygen levels.

Some embodiments of the present invention may include one, or more, of the following operations, features, characteristics and/or advantages: (i) record various assets and space restrictions within a facility; (ii) functional block reservation records are saved in a database (DB); (iii) the functional block reservation records includes at least some of, but not limited to, the following information: (a) functional block names, (b) functional block type (conference room, cubicle, classroom, etc.), (c) space needed (measured by "grid"), (d) technology resources needed in a functional block, (e) capacity needed (max number of the seats available in a functional block (such 1 for a cubicle, 10 for a conference room, and 50 for a classroom), (e) usage type (such as public or private), (f) booking type (one time booking or recurrently booking), (g) booking time (from when to when the functional block will be used), (h) a user identification (such as name, employee ID) who is booking the functional block, (i) attendees list of the event which this functional block will be used for, (j) number of people expected to join the event in person, (k) time stamp (for example, yy/mm/dd/minutes) of the booking record updated in the DB, (l) historical usage patterns for spaces, and (m) various amenities required such as: windows, whiteboards, projectors, etc.

Some embodiments of the present invention may include one, or more, of the following operations, features, characteristics and/or advantages: (i) a service to access a user's meeting requirements is used to calculate the demand of the functional blocks from each user in a given time frame (e.g.: "a business day"); (ii) for example, it can be a user's calendar (or any other information available which can provide user's schedule; (iii) some tracking technology, (such as hardware/sensors) needs to be available in the building; (iv) it will be used as the identification and tracking of the user and their activities; (v) such hardware/sensors may include at least some, but is not necessarily limited to, the following: (a) occupancy sensors, (b) cameras, (c) badge swipes, (d) desk sensors, (e) Bluetooth device detection sensors, (f) mobile device proximity sensors, (g) geo-location trackers, and (h) wi-fi data usage tracking; (vi) Privacy Adjustable Separators—similar to pocket window in a car, this can be controlled by an individual (if they have permission) or the grid-floor system; (vii) a service to calculate the demand of the different functional blocks for a given time frame (such as next day); (viii) based on each user's calendar, the system will calculate how may conference rooms, classrooms or cubicles are needed (one assumption that may be applied assumes if a person is not invited to a meeting, a class, then she and he will use cubicle space); (ix) an optimization service, based on the demand of the functional areas, will configure the grid floor setup by changing the height of "adjustable walls" to form different set of functional blocks based on a new optimized floor plan; (x) this optimization service can do so on demand or at a fixed schedule, such as every evening; (xi) users will be notified (such as by email, slack or calendar update) with a location map for the next day schedule; (xii) a location could be identified by floor and grid E-N index, see FIGS. 6-9, described below, where E-N refers to East-North block index, such as floor2-E3-N4; (xiii) an "Office Space Usage Map" can be shown on a web page or a public screen (such as a display at the entrance of the office space; and (xiv) see an example office space usage map in FIG. 9, described below.

Figure 5:
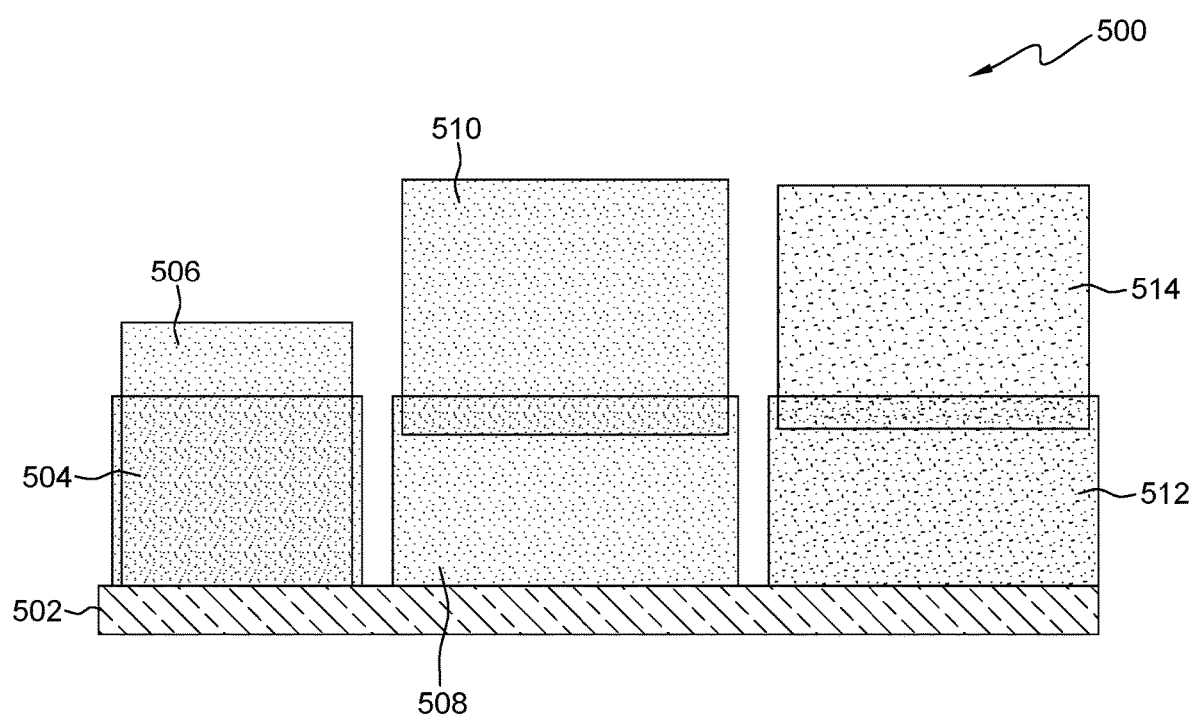
FIG. 5 is a block diagram of a dynamically adjustable privacy separator according to a second embodiment of the present invention.

An example retractable space divider retracting and adjusting opacity is shown in diagram 500 of FIG. 5. Connected to floor 502 are three example retractable space dividers comprising a lower portion (504, 508 and 512) and an upper portion (506, 510 and 514). Each lower and upper portion are made of a material with an electronically adjustable transparency/opacity level, such as in smart glass or switchable glass. While lower portion 512 and upper portion 514 are shown featuring smart glass that has been supplied an appropriate voltage to render them similarly transparent to typical glass, lower portions 504 and 508 as well as upper portions 506 and 512 are shown featuring smart glass that has been supplied an appropriate voltage to render them fully or nearly fully opaque.

An example second embodiment according to the present invention will now be discussed, with reference to FIGS. 6, 7, 8 and 9.

Figure 6:
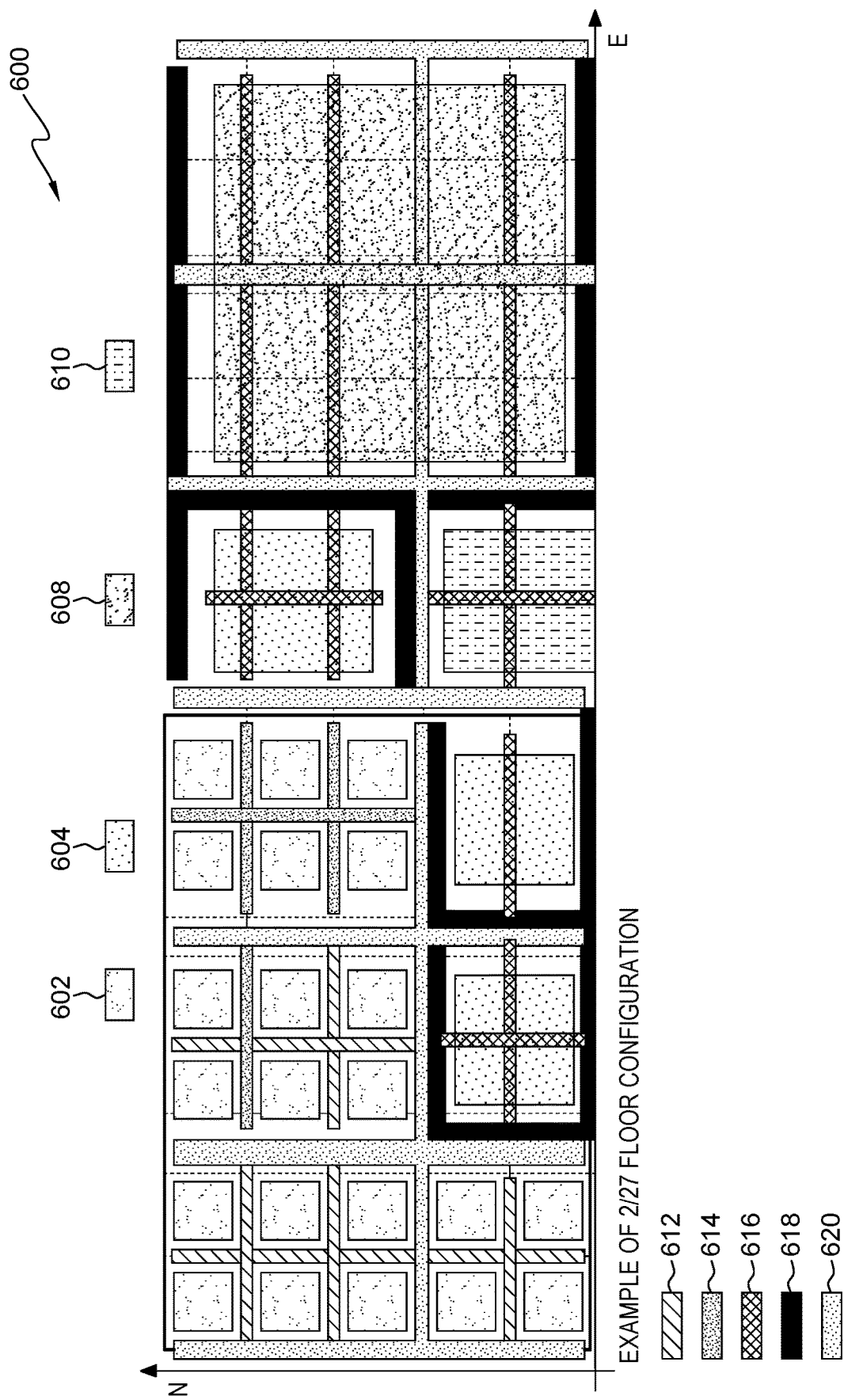
FIG. 6 is a screenshot view of a first floor plan generated by a second embodiment system of the present invention.
Figure 7:
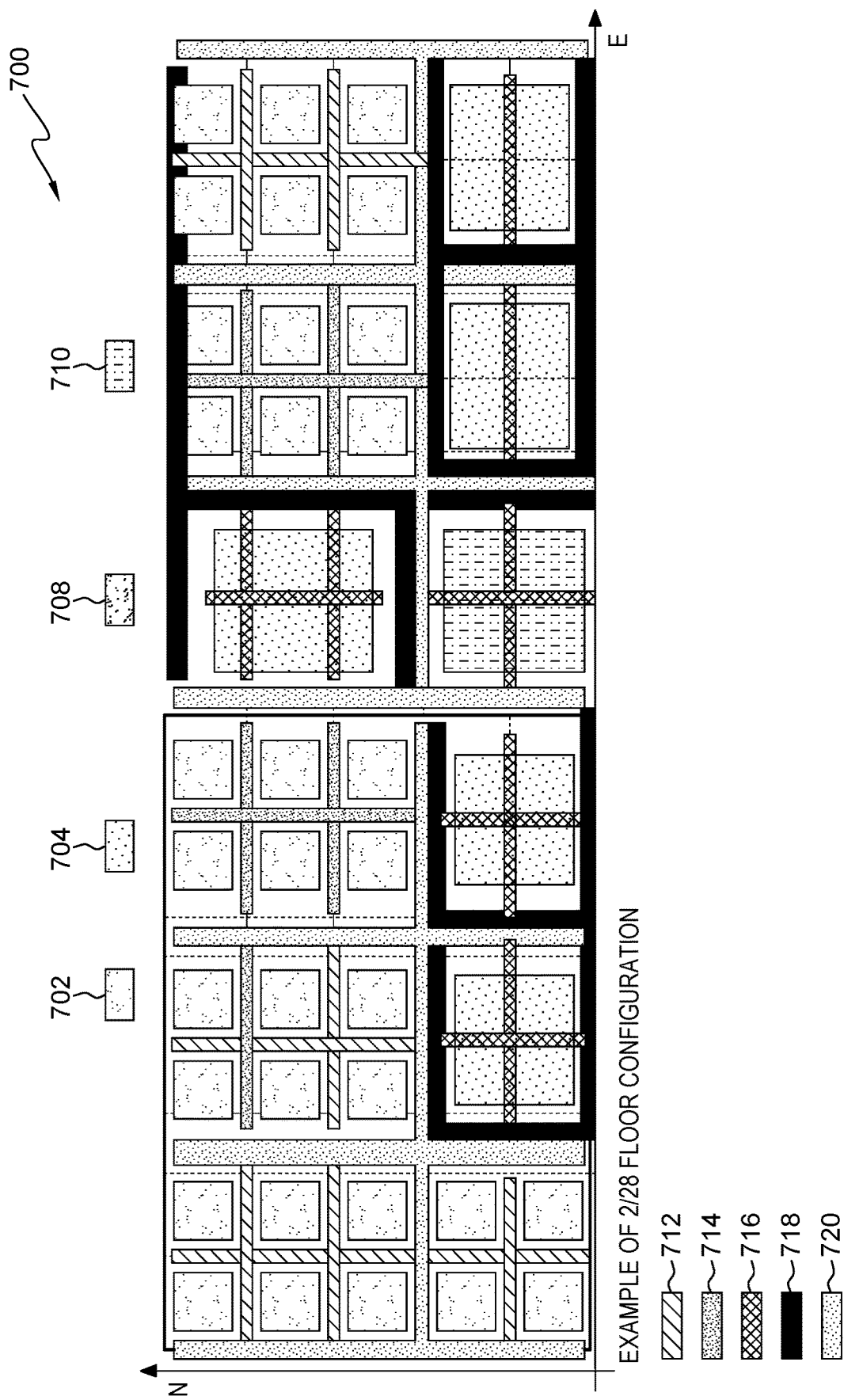
FIG. 7 is a screenshot view of a second floor plan generated by the second embodiment system of the present invention.
Figure 8:
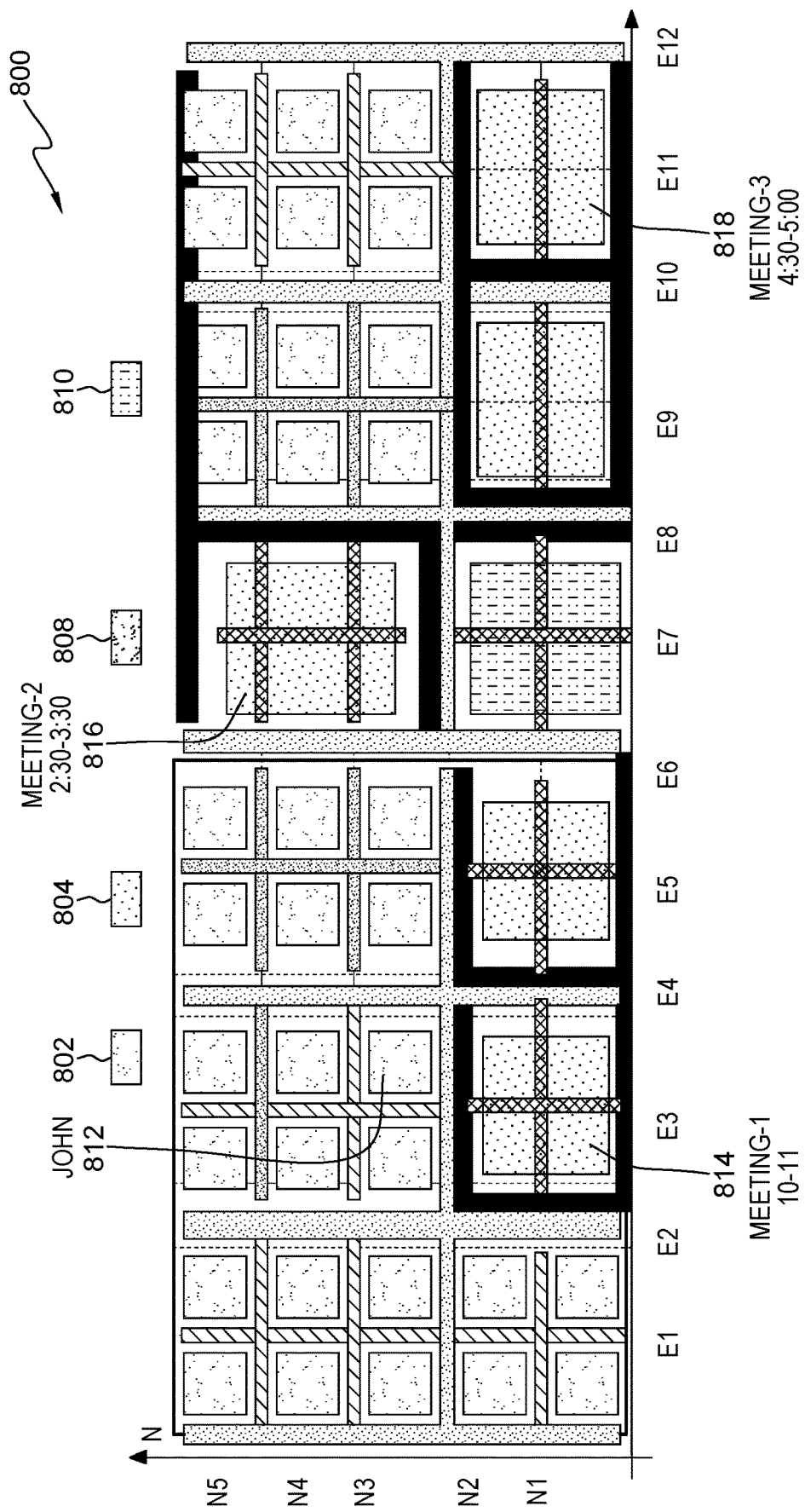
FIG. 8 is a screenshot view of a personal calendar shown as a floor plan generated by the second embodiment system of the present invention.

On the evening of Feb. 26, 2020, the system optimization service ran and generated an updated floor plan, as shown in screenshot 600 of FIG. 6, which includes: several cubicles (patterned as 602), 3 conference rooms (patterned as 604), one agile area (patterned as 610) and one large classroom (patterned as 608). A classroom was required that day because there was a full day AI class is scheduled in that building on February 27$^{th}$. Then the system control unit adjusted each privacy separators height and fade degree as shown in FIG. 6 (where 612 and 614 correspond to cubicle-height level privacy separators of full opacity and full transparency, respectively) to setup a new office space configuration. Additionally, 616 and 618 correspond to minimally and maximally raised privacy separators, with minimally raised separators fully retracted into the floor, and 620 corresponds to foot traffic routes. For some selected cubicle spaces, the system provides permission for each user to adjust privacy settings of the wall separator (height of the separator, degree of fade/opacity).

On the evening of Feb. 27, 2020, the system optimization service ran again and generated a new floor plan for the next day, Feb. 28, 2020, which was different from the floor plan as shown in FIG. 6. As shown in screenshot 700 of FIG. 7, the new floor plan includes more cubicles (patterned as 702), 5 conference rooms (patterned as 704) and one agile area (patterned as 710). No classrooms are included, which would be shown as pattern 708 if they were. Since there was no class scheduled on February 28$^{th}$, so the space that was one big classroom the previous day was divided into several cubicles and conference rooms. Similar to FIG. 6, 712 and 714 correspond to cubicle-height level privacy separators of full opacity and full transparency, respectively. Additionally, 716 and 718 correspond to minimally and maximally raised privacy separators, with minimally raised separators fully retracted into the floor, and 720 corresponds to foot traffic routes. For some selected cubicle spaces, the system provides permission for each user to adjust privacy settings of the wall separator (height of the separator, degree of fade/opacity).

On the morning of Feb. 28, 2020, John received a calendar update with meeting locations labelled on the map. A floorplan view of his calendar is shown in screenshot 800 of FIG. 8. John can pick any open cubicle he likes as his working space for that day. He is the first one to get into the office, so he picked floor2-N3-E4 as his office on February 28, right after he "parked" there, his name is labelled on the office map, as shown at 812. This office map can be shared on a public screen, such as near the entrance to the building or at each entrance to a relevant floor (such as the elevators and stairs on floor 2 of the building) so that persons entering the building or floor know which spaces are occupied and where everyone is located. As in the previous floorplans shown in FIGS. 6 and 7, cubicles are patterned as 802, conference rooms as 804, classrooms (though there are none on this day) as 808, and agile spaces as 810. John's floorplan view of his calendar shows his first meeting, Meeting-1 from 10-11, at 814, his second meeting, Meeting-2 from 2:30-3:30, at 816, and his third meeting, Meeting-3 at 4:30-5:00, at 818.

Figure 9:
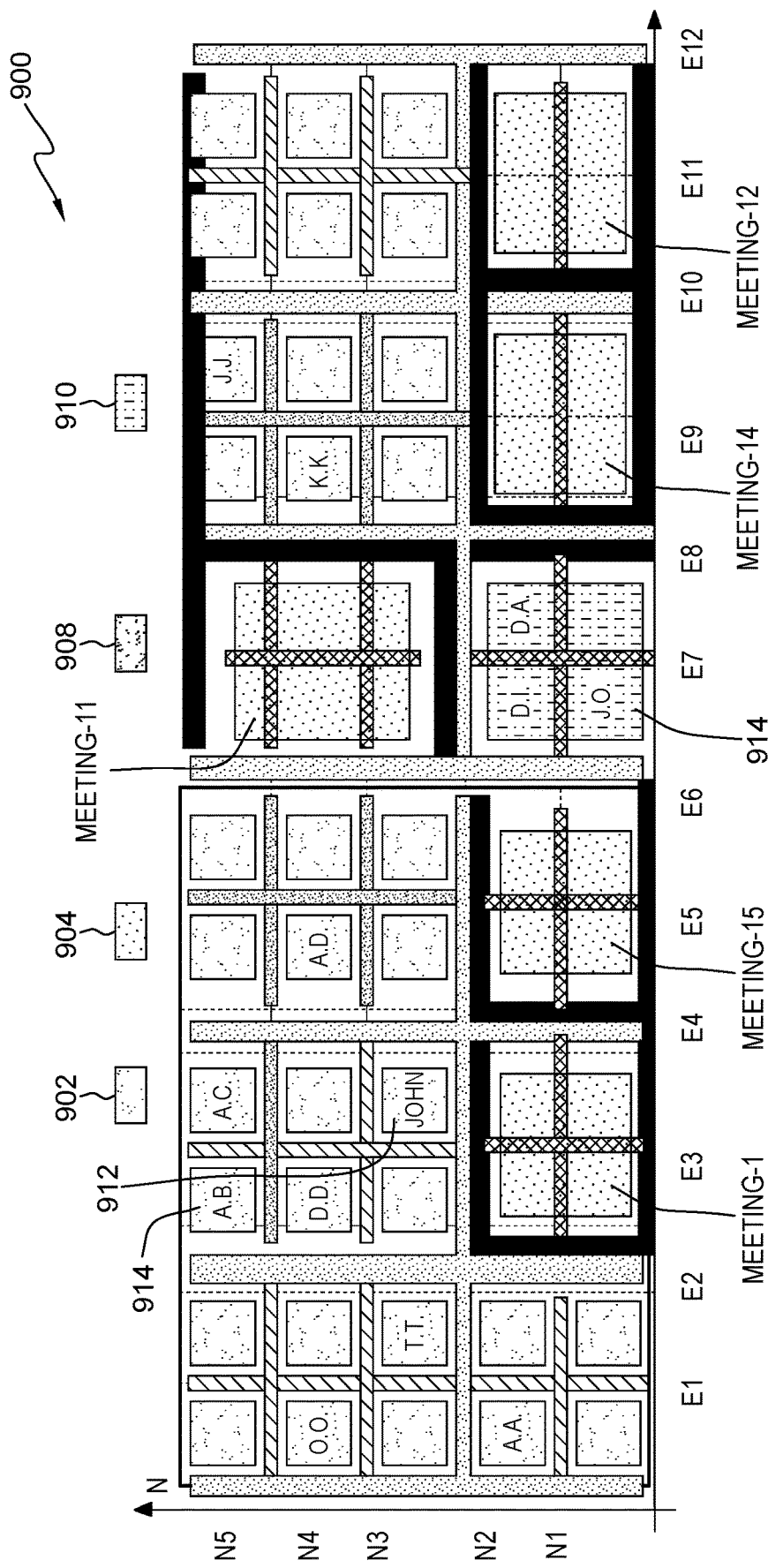
FIG. 9 is a screenshot view of a populated floor plan generated by the second embodiment system of the present invention.

At 11 AM on Feb. 28, 2020, most people have arrived at the office and "parked" at different cubicles, as shown in screenshot 900 of FIG. 9, which shows who was sitting where on the office map, which is dynamically updated based on the cameras or occupancy sensors. As in the previous floorplans shown in FIGS. 6, 7 and 8, cubicles are patterned as 902, conference rooms as 904, classrooms (though there are none on this day) as 908, and agile spaces as 910. John, who previously selected his cubicle as floor2-N3-E4 as his office on February 28, is shown at the same location as in FIG. 8, now shown as 912. Other people in the office have occupied various spaces, such as A. B. occupying cubicle floor2-N5-E3 (shown as 914), or J. O. occupying one of the spaces in the agile space occupying floor2-N1-E7 to floor2-N2-E8, or a two cubicle by two-cubicle floor space amounting to four square cubicles of floor space.

According to a third embodiment of the present invention, there is a method to dynamically adjust a building floor plan to meet varying business needs comprising: (i) receiving a list of usage requirements including people, space, technical resources, attributes, and in person meeting attendees; (ii) applying a trained meeting model to the list of usage requirements to form an adjusted building floor plan schedule tailored to meet a demand for a set of functional blocks; and (iii) performing actions to dynamically adjust the building floor plan based on the adjusted building floor plan schedule. The method according to the third embodiment, wherein the functional blocks are selected from a group consisting of conference rooms, cubicles, classrooms, office areas, and etc. The method according to the third embodiment, wherein the functional blocks are selected from a group consisting of conference rooms, cubicles, classrooms, office areas, etc. and the adjusted building floor plan schedule is for a plurality of periods of time allowing for supporting a first plan for a first period of time and a second plan for a second period time. The method according to the third embodiment, further comprising: providing adjustable privacy separators with height and fade [translucent to opaque] control. The method according to the third embodiment, further comprising: providing office [cubical] identifications, and a notification means for identifying changes and a current floor plan.

IV. DEFINITIONS

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

In an Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, and application-specific integrated circuit (ASIC) based devices.

Without substantial human intervention: a process that occurs automatically (often by operation of machine logic, such as software) with little or no human input; some examples that involve "no substantial human intervention" include: (i) computer is performing complex processing and a human switches the computer to an alternative power supply due to an outage of grid power so that processing continues uninterrupted; (ii) computer is about to perform resource intensive processing, and human confirms that the resource-intensive processing should indeed be undertaken (in this case, the process of confirmation, considered in isolation, is with substantial human intervention, but the resource intensive processing does not include any substantial human intervention, notwithstanding the simple yes-no style confirmation required to be made by a human); and (iii) using machine logic, a computer has made a weighty decision (for example, a decision to ground all airplanes in anticipation of bad weather), but, before implementing the weighty decision the computer must obtain simple yes-no style confirmation from a human source.

Automatically: without any human intervention.

What is claimed is:

1. A computer-implemented method (CIM) for use with a portion of floorspace of a building with a plurality of retractable privacy partitions throughout the portion of the floorspace, the CIM comprising:
   receiving a floorplan requirements dataset indicating floorspace requirements corresponding to quantities of at least one type of room needed within the portion of floorspace of the building;
   responsive to receiving occupancy input indicating occupancy of at least one room of the plurality of rooms, generating an occupied updated floorplan including information corresponding to which room of the plurality of rooms is occupied indicated by the occupancy input;
   responsive to generating the occupied updated floorplan: extending at least one of the retractable privacy partitions based, at least in part, on the occupancy input, and retracting at least one of the retractable privacy partitions based, at least in part, on the occupancy input; and determining an updated floorplan for the portion of floorspace of the building, based, at least in part, on the floorplan requirements dataset, where the updated floorplan includes a plurality of rooms of at least one type of room defined by at least partially extending at least one of the plurality of retractable privacy partitions and completely retracting at least one of the plurality of retractable privacy partitions.

2. The CIM of claim 1, further comprising:
extending at least one of the retractable privacy partitions based, at least in part, on the updated floorplan; and
retracting at least one of the retractable privacy partitions based, at least in part, on the updated floorplan.

3. The CIM of claim 1, further comprising:
outputting the occupied updated floorplan to at least one digital display connected to a computer device.

4. The CIM of claim 1, further comprising:
receiving a user details dataset corresponding to user detail records of a plurality of individuals;
responsive to the occupancy input indicating occupancy of two or more adjacent rooms, comparing user detail records of individuals occupying the two or more adjacent rooms; and
retracting at least one retractable privacy partition based, at least in part, on the comparison of user detail records.

5. The CIM of claim 1, wherein the retractable privacy partitions are primarily comprised of one of: (i) switchable glass, (ii) fabric, (iii) plastic, (iv) metal, and (v) wood.

6. The CIM of claim 1, wherein the floorplan requirements dataset indicates quantities for at least one of the following types of rooms: (i) cubicles with partially extended retractable privacy partitions, (ii) offices with fully extended retractable privacy partitions, (iii) conference rooms suitable for a plurality of simultaneous occupants, and (iv) large classroom rooms suitable for the plurality of simultaneous occupants.

7. The CIM of claim 1, further comprising:
receiving a health index dataset corresponding to at least one type of information indicative of health status of an individual human, where the health status indicates that the individual human is unhealthy, and the updated floorplan includes information indicative that at least one room is reserved for occupancy by the individual human; and
extending at least one partitions corresponding to the at least one room is reserved for occupancy by the individual human based, at least in part, on the health index.

8. A computer program product (CPP) for use with a portion of floorspace of a building with a plurality of retractable privacy partitions throughout the portion of the floorspace, the CPP comprising:
a machine readable storage device; and
computer code stored on the machine readable storage device, with the computer code including instructions for causing a processor(s) set to perform operations including the following:
receiving a floorplan requirements dataset indicating floorspace requirements corresponding to quantities of at least one type of room needed within the portion of floorspace of the building;
responsive to receiving occupancy input indicating occupancy of at least one room of the plurality of rooms, generating an occupied updated floorplan including information corresponding to which room of the plurality of rooms is occupied indicated by the occupancy input;
responsive to generating the occupied updated floorplan:
extending at least one of the retractable privacy partitions based, at least in part, on the occupancy input, and
retracting at least one of the retractable privacy partitions based, at least in part, on the occupancy input; and
determining an updated floorplan for the portion of floorspace of the building, based, at least in part, on the floorplan requirements dataset, where the updated floorplan includes a plurality of rooms of at least one type of room defined by at least partially extending at least one of the plurality of retractable privacy partitions and completely retracting at least one of the plurality of retractable privacy partitions.

9. The CPP of claim 8, wherein the computer code further includes instructions for causing the processor(s) set to perform the following operations:
extending at least one of the retractable privacy partitions based, at least in part, on the updated floorplan; and
retracting at least one of the retractable privacy partitions based, at least in part, on the updated floorplan.

10. The CPP of claim 8, wherein the computer code further includes instructions for causing the processor(s) set to perform the following operations:
outputting the occupied updated floorplan to at least one digital display connected to a computer device.

11. The CPP of claim 8, wherein the computer code further includes instructions for causing the processor(s) set to perform the following operations:
receiving a user details dataset corresponding to user detail records of a plurality of individuals;
responsive to the occupancy input indicating occupancy of two or more adjacent rooms, comparing user detail records of individuals occupying the two or more adjacent rooms; and
retracting at least one retractable privacy partition based, at least in part, on the comparison of user detail records.

12. The CPP of claim 8, wherein the computer code further includes instructions for causing the processor(s) set to perform the following operations:
receiving a health index dataset corresponding to at least one type of information indicative of health status of an individual human, where the health status indicates that the individual human is unhealthy, and the updated floorplan includes information indicative that at least one room is reserved for occupancy by the individual human; and
extending at least one partitions corresponding to the at least one room is reserved for occupancy by the individual human based, at least in part, on the health index.

13. A computer system (CS) for use with a portion of floorspace of a building with a plurality of retractable privacy partitions throughout the portion of the floorspace, the CS comprising:
a processor(s) set;
a machine readable storage device; and
computer code stored on the machine readable storage device, with the computer code including instructions for causing the processor(s) set to perform operations including the following:

receiving a floorplan requirements dataset indicating floorspace requirements corresponding to quantities of at least one type of room needed within the portion of floorspace of the building;

responsive to receiving occupancy input indicating occupancy of at least one room of the plurality of rooms, generating an occupied updated floorplan including information corresponding to which room of the plurality of rooms is occupied indicated by the occupancy input;

responsive to generating the occupied updated floorplan:
- extending at least one of the retractable privacy partitions based, at least in part, on the occupancy input, and
- retracting at least one of the retractable privacy partitions based, at least in part, on the occupancy input; and
- determining an updated floorplan for the portion of floorspace of the building, based, at least in part, on the floorplan requirements dataset, where the updated floorplan includes a plurality of rooms of at least one type of room defined by at least partially extending at least one of the plurality of retractable privacy partitions and completely retracting at least one of the plurality of retractable privacy partitions.

14. The CS of claim 13, wherein the computer code further includes instructions for causing the processor(s) set to perform the following operations:

extending at least one of the retractable privacy partitions based, at least in part, on the updated floorplan; and retracting at least one of the retractable privacy partitions based, at least in part, on the updated floorplan.

15. The CS of claim 13, wherein the computer code further includes instructions for causing the processor(s) set to perform the following operations:

outputting the occupied updated floorplan to at least one digital display connected to a computer device.

16. The CS of claim 13, wherein the computer code further includes instructions for causing the processor(s) set to perform the following operations:

receiving a user details dataset corresponding to user detail records of a plurality of individuals;

responsive to the occupancy input indicating occupancy of two or more adjacent rooms, comparing user detail records of individuals occupying the two or more adjacent rooms; and retracting at least one retractable privacy partition based, at least in part, on the comparison of user detail records.

17. The CS of claim 13, wherein the computer code further includes instructions for causing the processor(s) set to perform the following operations:

receiving a health index dataset corresponding to at least one type of information indicative of health status of an individual human, where the health status indicates that the individual human is unhealthy, and the updated floorplan includes information indicative that at least one room is reserved for occupancy by the individual human; and extending at least one partitions corresponding to the at least one room is reserved for occupancy by the individual human based, at least in part, on the health index.

* * * * *